United States Patent [19]
Sullenperger et al.

[11] Patent Number: 5,916,189
[45] Date of Patent: Jun. 29, 1999

[54] NECK FIXING APPARATUS

[75] Inventors: Peter C. Sullenperger, Seattle, Wash.; Masaaki Sakuma; Kenji Suzuki, both of Tokyo, Japan; Kazuhiko Hayakawa, Kanagawa, Japan; Yasushi Kato, Tokyo, Japan

[73] Assignee: GE Yokogawa Medical Systems, Limited, Tokyo, Japan

[21] Appl. No.: 08/994,909

[22] Filed: Dec. 19, 1997

[51] Int. Cl.⁶ ........................................ A61F 5/00
[52] U.S. Cl. ................................. 602/36; 602/32
[58] Field of Search .............. 602/5, 6, 17–19, 602/32, 36; 128/845, 869, DIG. 23

[56] References Cited

U.S. PATENT DOCUMENTS

| | | | |
|---|---|---|---|
| 4,485,808 | 12/1984 | Hepburn | 602/5 |
| 5,081,665 | 1/1992 | Kostich | 5/637 |
| 5,088,482 | 2/1992 | McGuinness | 602/18 |
| 5,302,170 | 4/1994 | Tweardy | 602/17 |
| 5,437,619 | 8/1995 | Malewicz et al. | 602/20 |
| 5,541,515 | 7/1996 | Tsujita . | |

*Primary Examiner*—Richard J. Apley
*Assistant Examiner*—Denise Pothier
*Attorney, Agent, or Firm*—Moonray Kojima

[57] ABSTRACT

For the purpose of supporting the subject's head corresponding to the motion of the subject's neck, there is provided a neck fixing apparatus comprising a base disposed on a surface on which the subject is mounted, an arm extending along the body axis of the subject to be mounted and pivotally attached to the base, and a head rest 82 for mounting the subject's head, movably attached to the arm and movable along the arm 60.

1 Claim, 14 Drawing Sheets

NECK FIXING APPARATUS

BACKGROUND OF THE INVENTION

The present invention relates to a fixing apparatus for fixing the neck of a subject.

In recent MRI (Magnetic Resonance Imaging) apparatuses, the diameter of the bore is made larger to allow physicians to diagnose a subject in various positions.

When the imaging of the subject's neck bone is required under the condition that the subject's neck is bent at various angles, a neck fixing apparatus shown in FIG. 1 is used.

Referring to FIG. 1 (a), there is shown a perspective view of the prior-art neck fixing apparatus, wherein a base portion 2 disposed on a surface on which the subject is mounted is provided with a head support 4 for mounting the subject's head, and the head support 4 is attached using threads 6.

In the above-constructed neck fixing apparatus, the head support 4 is rotated with respect to the base portion 2 by loosening the threads 6, and maintained at a selected position by driving the threads 6.

FIG. 1 (b) is a view taken in the direction indicated by arrow A in FIG. 1 (a), wherein the neck fixing apparatus is put on the subject. As shown in FIG. 1 (b), the head support 4 is provided with a cushioning material (pad) 8, and the subject's head 10 is mounted on the cushioning material 8 and fixed to the head support 4 using a band 12 fitting on the forehead.

Although the neck is similar to other joints such as the elbow, knee, wrist or ankle in that they are movable, it is different from the other joints in some ways. That is, the joint at the elbow, knee, wrist, ankle or the like is moved with its center of rotation fixed, whereas the neck consisting of seven cervical vertebrae is moved with its center of rotation varied because the individual vertebrae are moved separately.

When the subject's neck is bent at various angles using the neck fixing apparatus constructed as shown in FIG. 1, the motion of the subject's neck bone which has varying centers of rotation does not match with the motion of the head support 4 which has a fixed center of rotation.

Therefore, discordance occurs between the subject's head 10 and the head support 4, resulting in problems that the band 12 gets off from the subject's head 10 and/or touches the subject's eyes or nose.

SUMMARY OF THE INVENTION

It is an object of the present invention to provide a neck fixing apparatus in which the motion of the neck and that of the head support matches with each other.

In accordance with one aspect of the present invention, there is provided a neck fixing apparatus comprising a base disposed on a surface on which a subject is mounted, arm portions extending along the body axis of the subject to be mounted, pivotally attached to the base, and rotatable around the respective proximal ends of the arm portions, and a head support for mounting the subject's head, movably attached to the arm portions, and movable along the direction in which the arm portion extends.

Since the head support on which the subject's head is mounted is moved along the arm portions in conjunction with the rotation of the arm portions, the discordance between the subject's head and the head support is avoided and the motion of the head support and that of the subject's head match with each other.

In a second aspect of the present invention, there is provided a neck fixing apparatus in accordance with the first aspect, wherein the head support is rotatable around an axis extending in the direction orthogonal to the body axis of the subject and lying within a plane parallel to the surface of the base.

When the subject's neck needs to be rotated to a substantial extent, the subject's head may be brought close to an inner peripheral surface of the bore in the MRI apparatus and the additional rotation of the arm portions may cause the subject's head to meet the inner peripheral surface of the bore in the MRI apparatus. In such a case, the additional rotation of the subjects' neck can be accomplished by rotating the head support with respect to the arm portions, preventing the subject's head and the inner peripheral surface of the bore in the MRI apparatus from touching each other.

In a third aspect of the present invention, there is provided a neck fixing apparatus in accordance with the first and second aspects, wherein the arm portions as a whole are movable in the direction orthogonal to the surface of the base.

When the subject's neck needs to be rotated to a substantial extent, the subject's head may be brought close to the inner peripheral surface of the bore in the MRI apparatus and the additional rotation of the arm portions may cause the subject's head to meet the inner peripheral surface of the bore in the MRI apparatus. In such a case, the additional rotation of the subject's neck can be accomplished by moving the arm portions upwardly or downwardly with respect to the surface of the base, preventing the subject's head and the inner peripheral surface of the bore in the MRI apparatus from touching each other.

When the neck fixing apparatus in accordance with the present invention is used in an MRI apparatus, the subject's head is supported on the head support at first. The arm portions are then rotated, with the head support maintained movable with respect to the arm portions. Thus, the head support is moved along the arm portions in conjunction with the rotation of the arm portions, and as a result, the discordance between the subject's head and the head support is avoided and the motion of the head support and that of the subject's head match with each other.

Moreover, when the subject's neck needs to be rotated to a substantial extent, the subject's head may be brought close to the inner peripheral surface of the bore in the MRI apparatus and the additional rotation of the arm portions may cause the subject's head to meet the inner peripheral surface of the bore in the MRI apparatus. In such a case, the additional rotation of the subject's neck can be accomplished by rotating the head support with respect to the arm portions and/or by moving the arm portions in the direction generally orthogonal to the base, preventing the subject's head and the inner peripheral surface of the bore in the MRI apparatus from touching each other.

Further objects and advantages of the present invention will be apparent from the following description of the preferred embodiments of the invention as illustrated in the accompanying drawings.

BRIEF DESCRIPTION OF THE DRAWINGS

FIG. 1B illustrates a cross sectional view of use of the device of FIG. 1A with a subject's head held thereon.

DETAILED DESCRIPTION OF THE INVENTION

One embodiment of the present invention will be described with reference to the accompanying drawings.

Figure 1B:
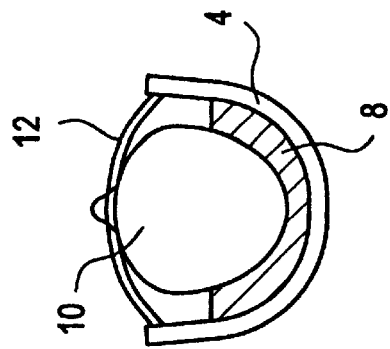
FIGS. 1A and 1B illustrates a prior-art neck fixing apparatus.
Figure 1A:
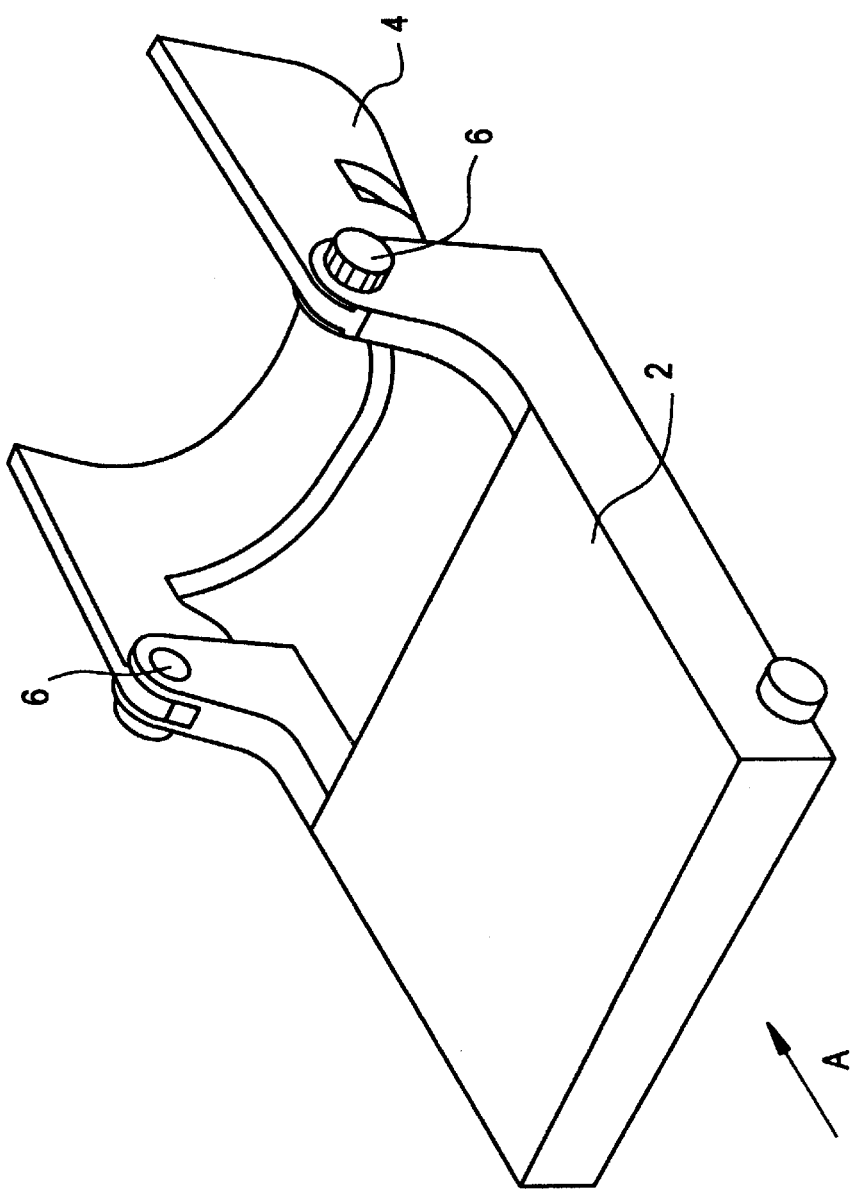
Figure 2:
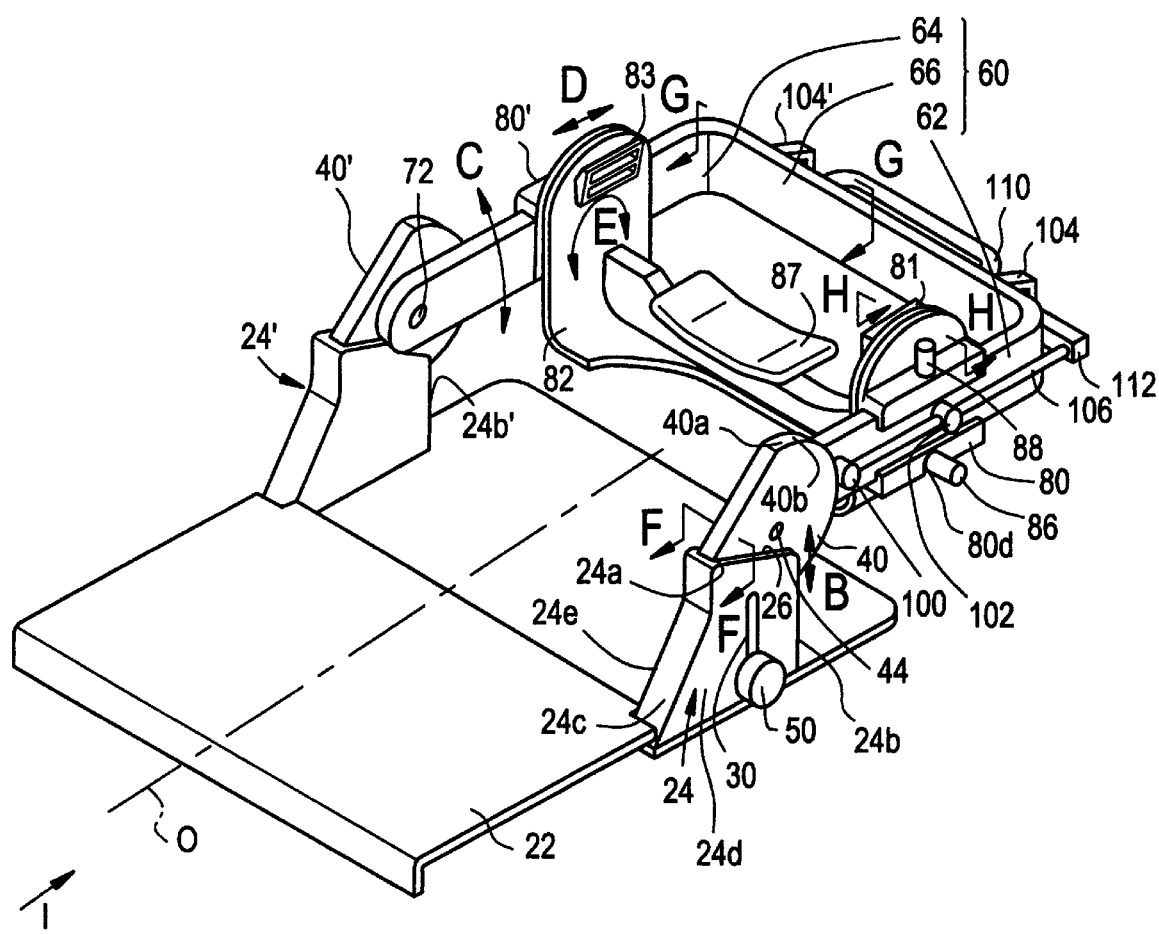
FIG. 2 is a perspective view of a neck fixing apparatus in accordance with one embodiment of the present invention.

Since a neck fixing apparatus in accordance with the embodiment is axisymmetric with respect to the body axis O of a subject to be mounted, the right side of the axis O in FIG. 2 will be particularly described, with the repeated description of the left side of the axis O omitted and reference numerals designating the components on the left side suffixed with "'" (prime).

(1) Overall arrangement

The overall arrangement of a neck fixing apparatus in accordance with one embodiment of the present invention will be described with reference to FIG. 2 which is a perspective view of a head supporting apparatus in accordance with the embodiment of the present invention.

A base 22 disposed on a surface on which a subject is mounted is provided with posts 24 and 24' standing on both sides. The posts 24 and 24' are provided with first sliding members 40 and 40', respectively. The first sliding members 40 and 40' are positioned so that they can be moved in the direction generally orthogonal to the base 22, i.e., in the direction indicated by arrow B in the drawing.

The first sliding members 40 and 40' are also provided with an arm 60 generally having a square C-shape. The arm 60 is comprised of first and second arm portions 62 and 64 with their proximal ends pivotally attached to the first sliding members 40 and 40', respectively, and a bridge 66 connecting the distal ends of the first and second arm portions 62 and 64. The arm 60 can be rotated in the direction indicated by arrow C in the drawing.

Also, a head rest 82 which serves as a head support for mounting the subject's head is positioned between the first and second arm portions 62 and 64 of the arm 60. The head rest 82 is attached so that it can be moved along the first and second arm portions 62 and 64 (i.e., in the direction indicated by arrow D in the drawing), and also can be rotated with respect to the first and second arm portions 62 and 64 (i.e., in the direction indicated by arrow E in the drawing).

Moreover, the head rest 82 is provided with a cushion 87 in the center for supporting the subject's head, and band stoppers 81 and 83 on the opposite sides for holding a band which fixes the subject's head to be mounted.

(2) Attachment of the posts 24 and 24' with the first sliding members 40 and 40'

Figure 3:
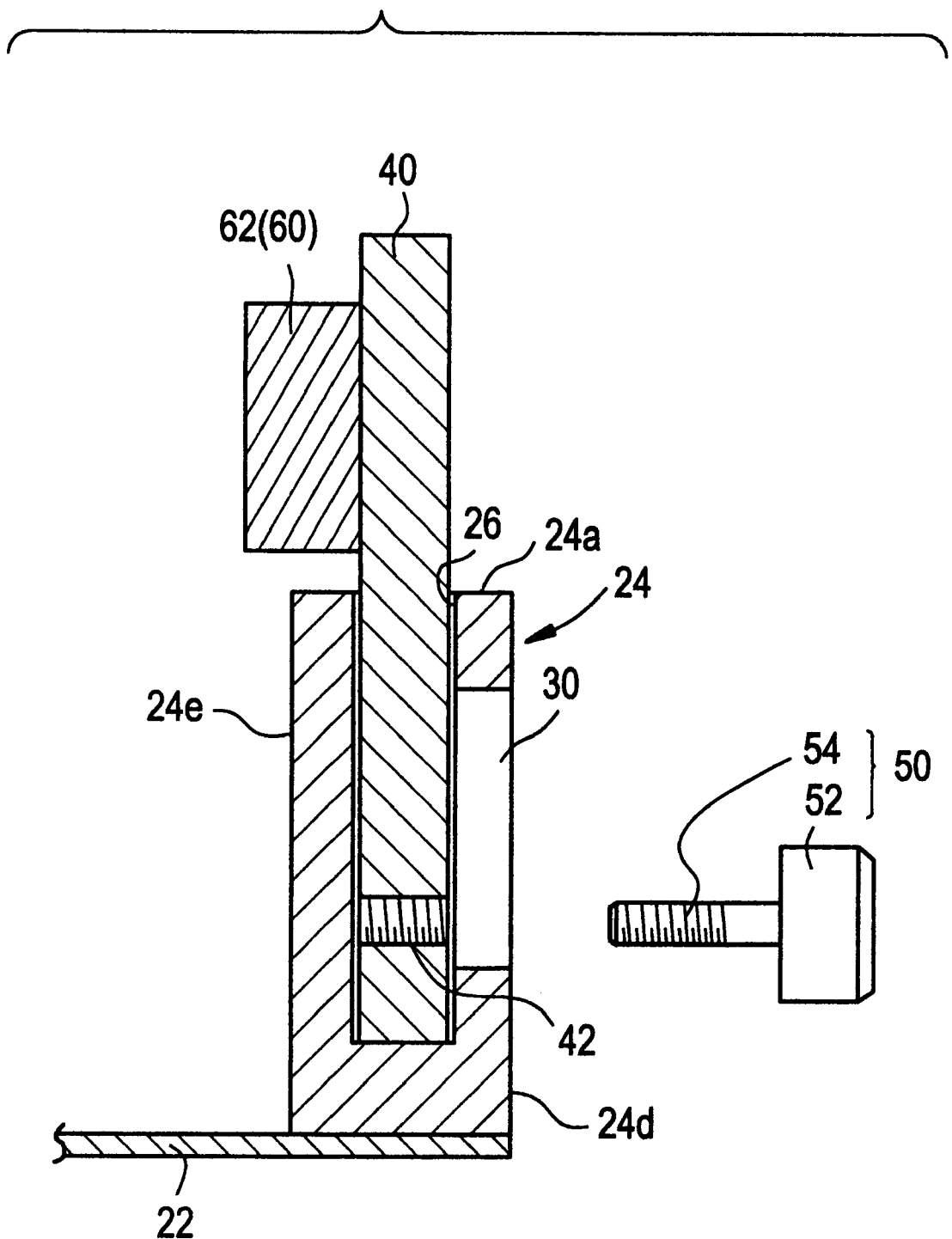
FIG. 3 is a cross-sectional view taken along the line F—F in FIG. 2.

The description is made with reference to FIGS. 2 and 3. FIG. 3 is a cross-sectional view taken along the line F—F in FIG. 2. As shown in FIG. 2, the post 24 has a top surface 24a, and lateral surfaces 24b and 24c intersecting the body axis O of the subject to be mounted, and is formed with a slit 26 having an opening in the top surface 24a and in the lateral surface 24b of the lateral surfaces 24b and 24c which lies nearer to the subject's head.

The post 24 also has other lateral surfaces 24d and 24e generally along the body axis O of the subject to be mounted, and the lateral surface 24d opposite to the lateral surface 24e adjacent to the subject is formed with a long hole 30 extending in the direction orthogonal to the base 22 (in the up-and-down direction) and penetrating into the slit 26.

On the other hand, as shown in FIG. 3, the lower portion of the first sliding member 40 is fitted into the slit 26 so that the first sliding member 40 can be moved upwardly and downwardly along the slit 26.

A part of the first sliding member 40 which is located inside the slit 26 is formed with an internal thread hole 42 extending generally parallel to the base 22.

In addition, there is provided a knob 50 comprised of a head portion 52 having a diameter larger than the width of the long hole 30 in the post 24, and an external thread 54 extending from the head portion 52. With the external thread 54 passing through the long hole 30 and threaded into the internal thread hole 42 in the first sliding member 40, and with the head portion 52 bearing against the lateral surface 24d of the post 24, the movement of the first sliding member 40 is prohibited.

(3) Attachment of the arm 60 and the first sliding member 40

Figure 4:
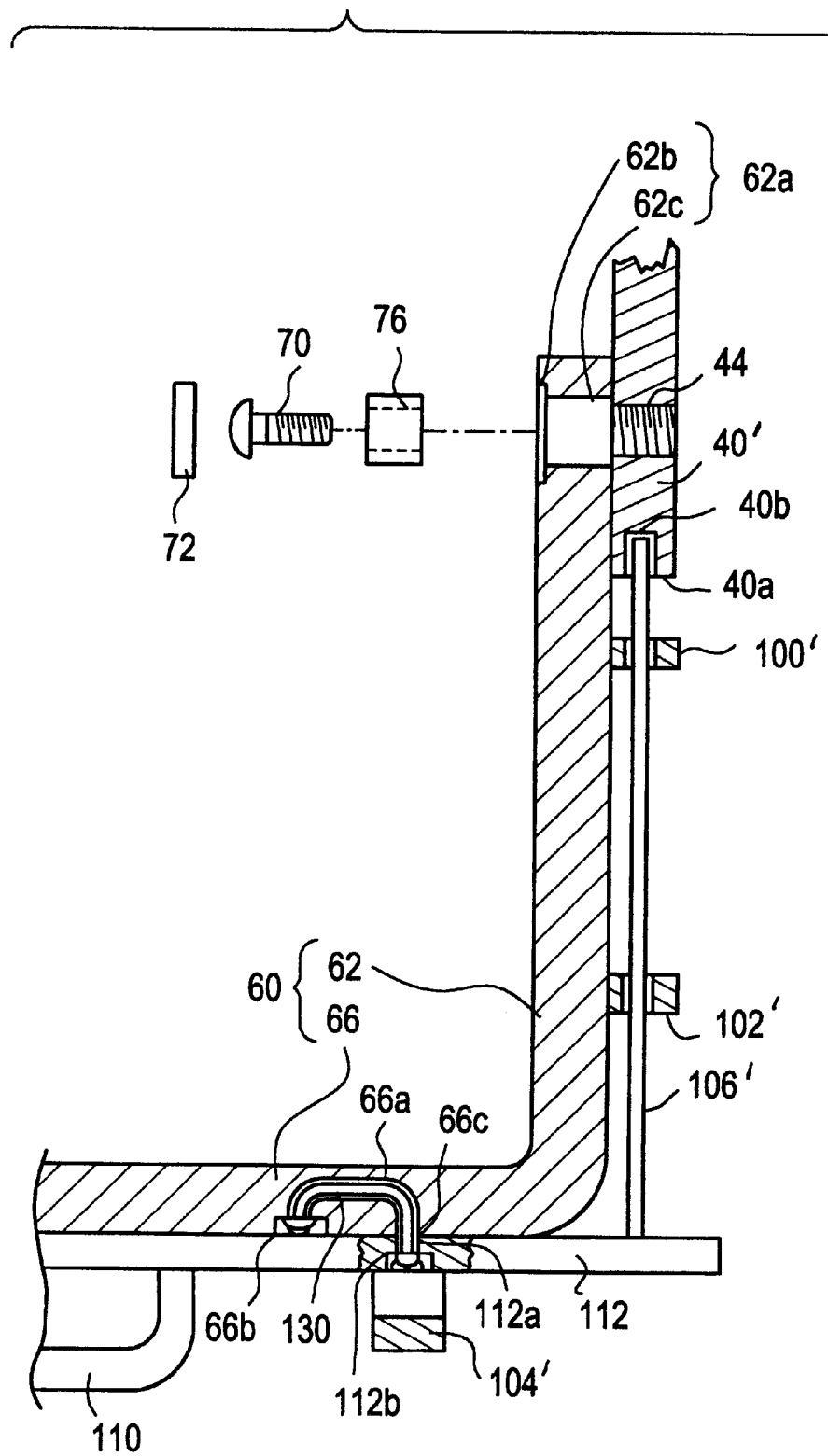
FIG. 4 is a cross-sectional view taken along the line G—G in FIG. 2.

The description is made with reference to FIGS. 2 and 4. FIG. 4 is a cross-sectional view taken along the line G—G in FIG. 2.

As shown in FIG. 4, the proximal end portion of the first arm portion 62 is formed with a through hole 62a comprised of a large diameter portion 62b and a small diameter portion 62c and having a step. On the other hand, the first sliding member 40 is formed with a threaded through hole 44.

A cylindrical spacer 76 is fitted into the small diameter portion 62c of the through hole 62a in the first arm portion 62, and the first arm portion 62 is pivotally attached to the first sliding member 40 by a thread 70 passing through the spacer 76 and threaded into the treaded through hole 44 in the first sliding member 40. According to this embodiment, the head portion of the thread 70 is covered with a facing cover 72 fitted into the large diameter portion 62b of the through hole 62a.

In addition, as shown in FIG. 2, the upper portion of the first sliding member 40 is formed with an arc-shaped peripheral surface 40a centering the threaded through hole 44. A plurality of lock holes 40b are provided at certain intervals on the peripheral surface 40a.

Each of the first and second arm portions 62 and 64 of the arm 60 is provided with a locking rod 106 supported by guide members 100 and 102 so that the locking rod 106 can be moved along the first and second arm portions 62 and 64 of the arm 60.

A first end of the locking rod 106 is engageable with either of the plurality of the lock holes 40b formed on the peripheral surface 40a of the first sliding member 40.

The bridge 66 of the arm 60 is provided with a handle 110 in the intermediate portion and a handle bar 112 supported by guide members 104 and 104' so that the handle bar 112 can be moved in the same direction as the movement direction of the locking rods 106 and 106', i.e., the handle bar 112 can be brought closer to/farther from the bridge 66.

In addition, the handle bar 112 is connected to second ends of the locking rods 106 and 106', and the handle bar 112 and the locking bar 106, 106' are integrated.

As shown in FIG. 4, the bridge 66 of the arm 60 is formed on each side with a generally U-shaped hole 66a having two openings 66b and 66c. Also, the handle bar 112 is formed with a hole 112a opposing to one opening 66c of the hole 66a in the arm 60.

The handle bar 112 is biased toward the bridge 66 of the arm 60 bearing against the bridge 66 by a linear elastic member 130 such as an elastic cord, one end of which is caught at the opening 66b of the arm 60, the intermediate portion thereof passing through the hole 66a of the arm 60 and also through the hole 112a of the handle bar 112, and the other end thereof being caught at an opening 112b of the hole 112a. According to the present embodiment, the catch of the elastic member 130 at the openings 66b and 112b is done by making knots at the either end of the elastic member 130 so that the ends of the elastic member 130 are made larger than the diameter of the hole 66a in the arm 60 and that of the hole 112a in the handle bar 112.

The length of the locking rod 106 is determined so that the rod 106 engages with the lock hole 40b in the first sliding member 40 when the handle bar 112 bears against the bridge 66 of the arm 60. The rotation of the arm 60 around the thread 70 is thus prohibited under the natural condition of the elastic member 130.

When the handle bar 112 is moved away from the bridge 66 of the arm 60 against the contractile force of the elastic member 130, the engagement of the locking rod 106 with the lock hole 40b in the first sliding member 40 is released. Thus, the rotation of the arm 60 around the thread 70 is allowed.

(4) Attachment of the head rest 82 and the arm 60

Figure 5:
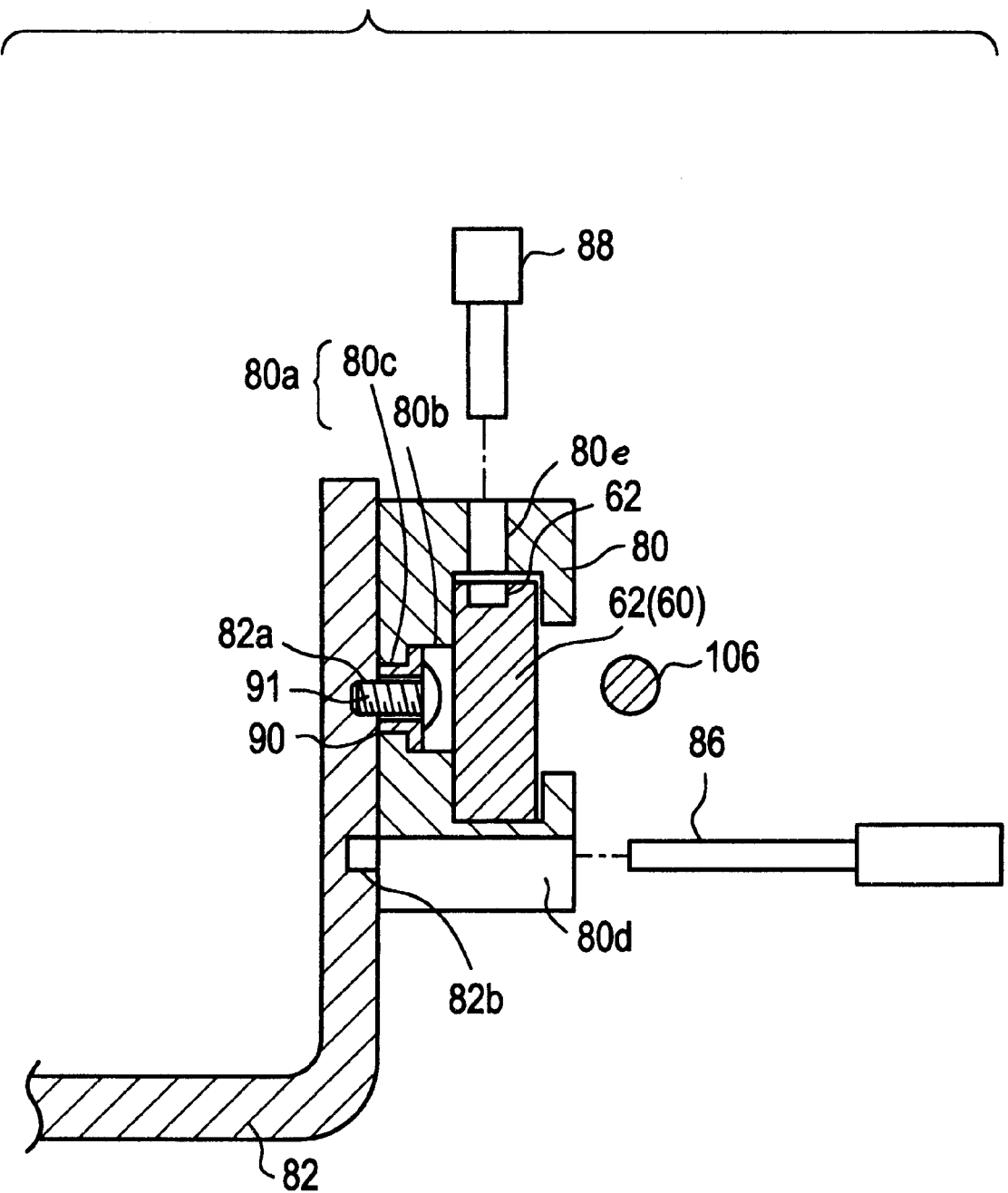
FIG. 5 is a cross-sectional view taken along the line H—H in FIG. 2.
Figure 6:
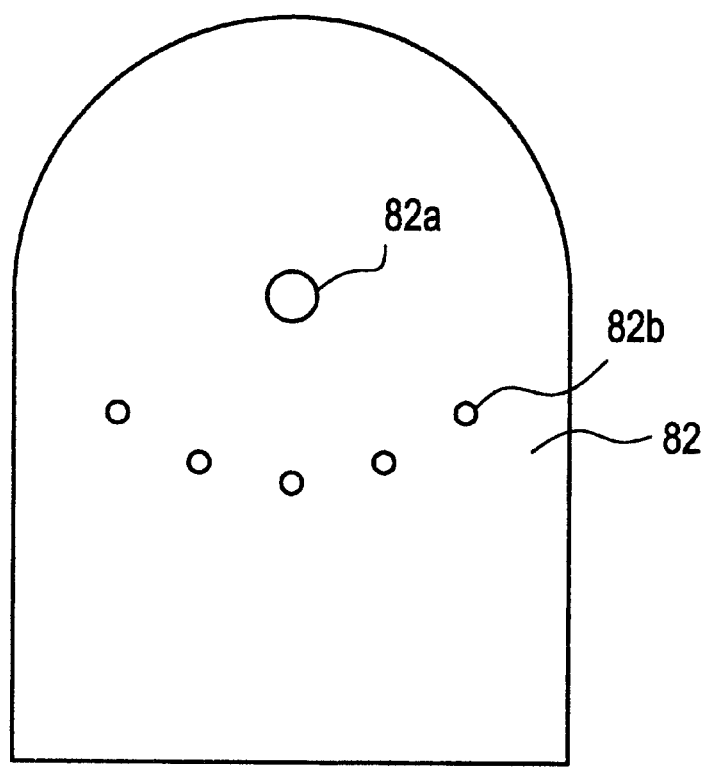
FIG. 6 is a side view of a head rest shown in FIG. 2.
Figure 7:
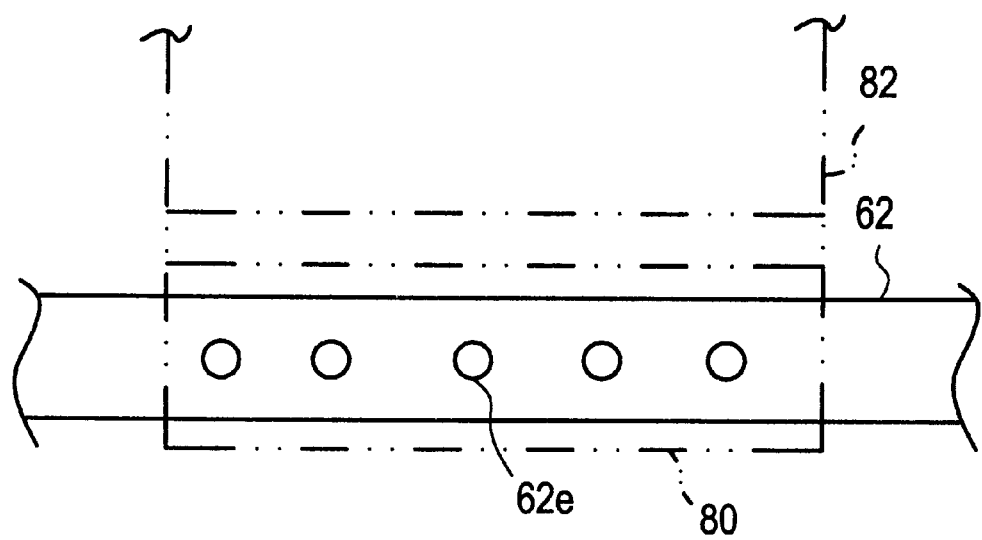
FIG. 7 is a top plan view of a sliding portion of a first arm portion of an arm shown in FIG. 2.

The description is made with reference to FIGS. 2, 5, 6 and 7. FIG. 5 is a cross-sectional view taken along the line H—H in FIG. 2, FIG. 6 illustrates the lateral surface of the head rest shown in FIG. 2, and FIG. 7 is a top plan view of a sliding portion of the first arm portion of the arm shown in FIG. 2.

As shown in FIG. 2, second sliding members 80 and 80' each having a generally C-shaped cross-section are engaged with the first and second arm portions 62 and 64 of the arm 60, respectively, so that the sliding members 80 and 80' can be moved along the first and second arm portions 62 and 64. And the head rest 82 serving as a head support on which the subject's head is mounted is positioned between the second sliding members 80 and 80'.

As shown in FIG. 5, a surface of the second sliding member 80 which is opposite to the head rest 82 is formed with a through hole 80a comprised of a large diameter portion 80b and a small diameter portion 80c.

On the other hand, the head rest 82 is formed with a threaded hole 82a opposing to the through hole 80a in the second sliding member 80.

A cylindrical flanged spacer 90 is fitted into the small diameter portion 80c of the through hole 80a in the second sliding member 80, and the head rest 82 is pivotally attached to the second sliding member 80 by a thread 91 as a pivot which passes through the spacer 90 and is threaded into the threaded hole 82a in the head rest 82.

In addition, a bottom surface of the second sliding member 80 is formed with a gutter 80d extending toward the head rest 82. On the other hand, as shown in FIG. 6, the head rest 82 is formed with a plurality of a lock holes 82b which are formed on a circumference centering the threaded hole 82a and are opposable to the gutter 80d in the second sliding member 80.

Thus, by inserting/removing a first locking pin 86 through the gutter 80d in each of the second sliding members 80 and 80' into/from one of the lock holes 82b in the head rest 82, the rotation of the head rest 82 around the thread 91 is prohibited/allowed, respectively.

A top surface of the second sliding member 80 is formed with a through hole 80e as shown in FIG. 5. On the other hand, as shown in FIG. 7, top surfaces of the first and second arm portions 62 and 64 of the arm 60 are formed with a plurality of lock holes 62e, each of which is opposable to the through hole 80e in the second sliding member 80.

Figure 11:
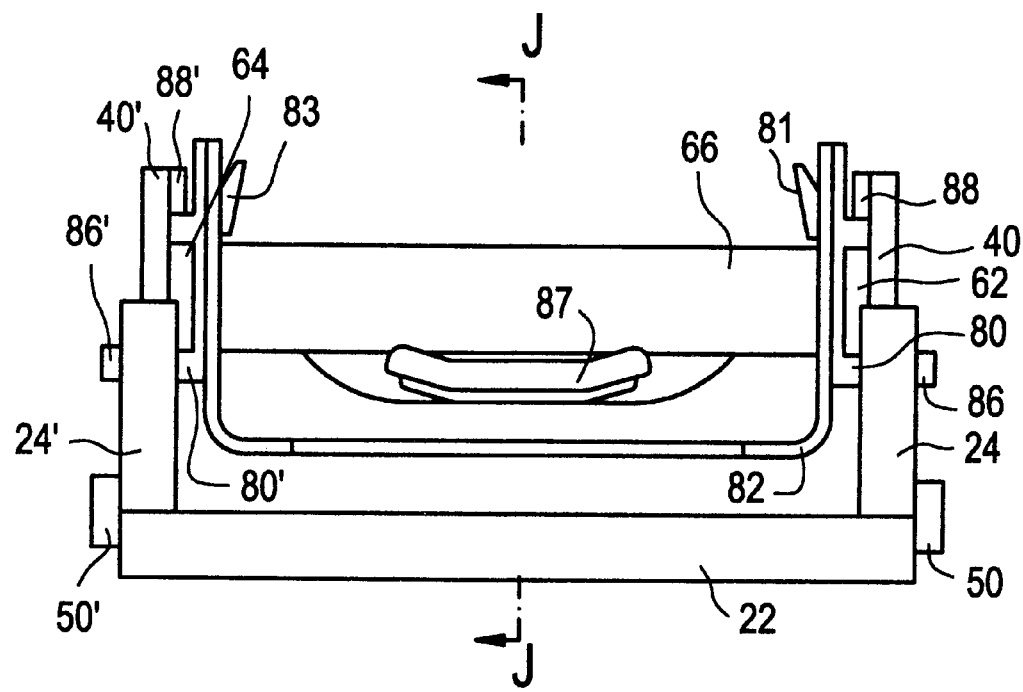
FIG. 11 is an elevational view taken in the direction indicated by arrow I in FIG. 2.
Figure 12:
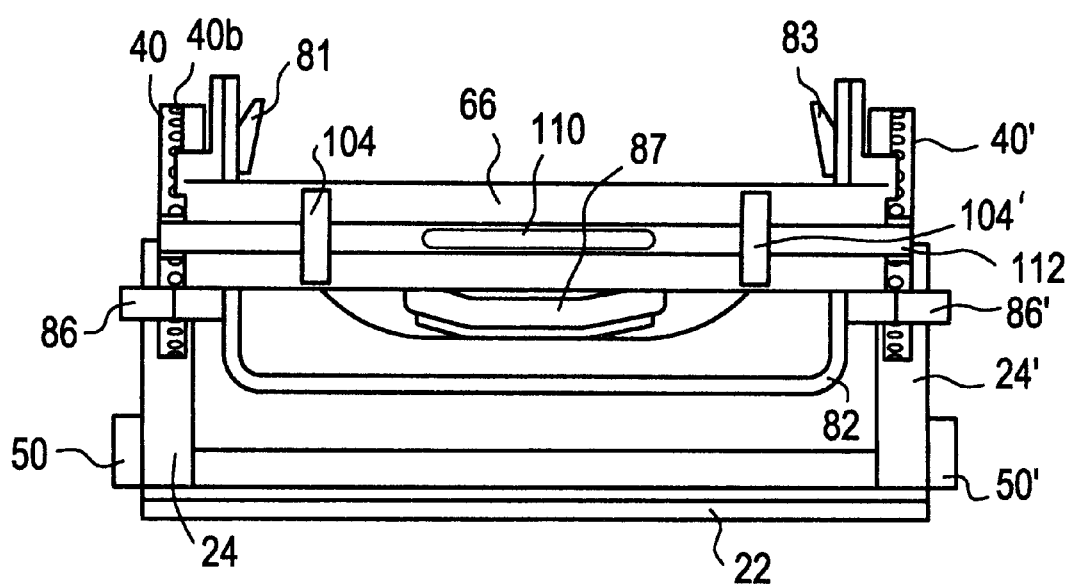
FIG. 12 is a back elevational view taken in connection with FIG. 11.
Figure 13:
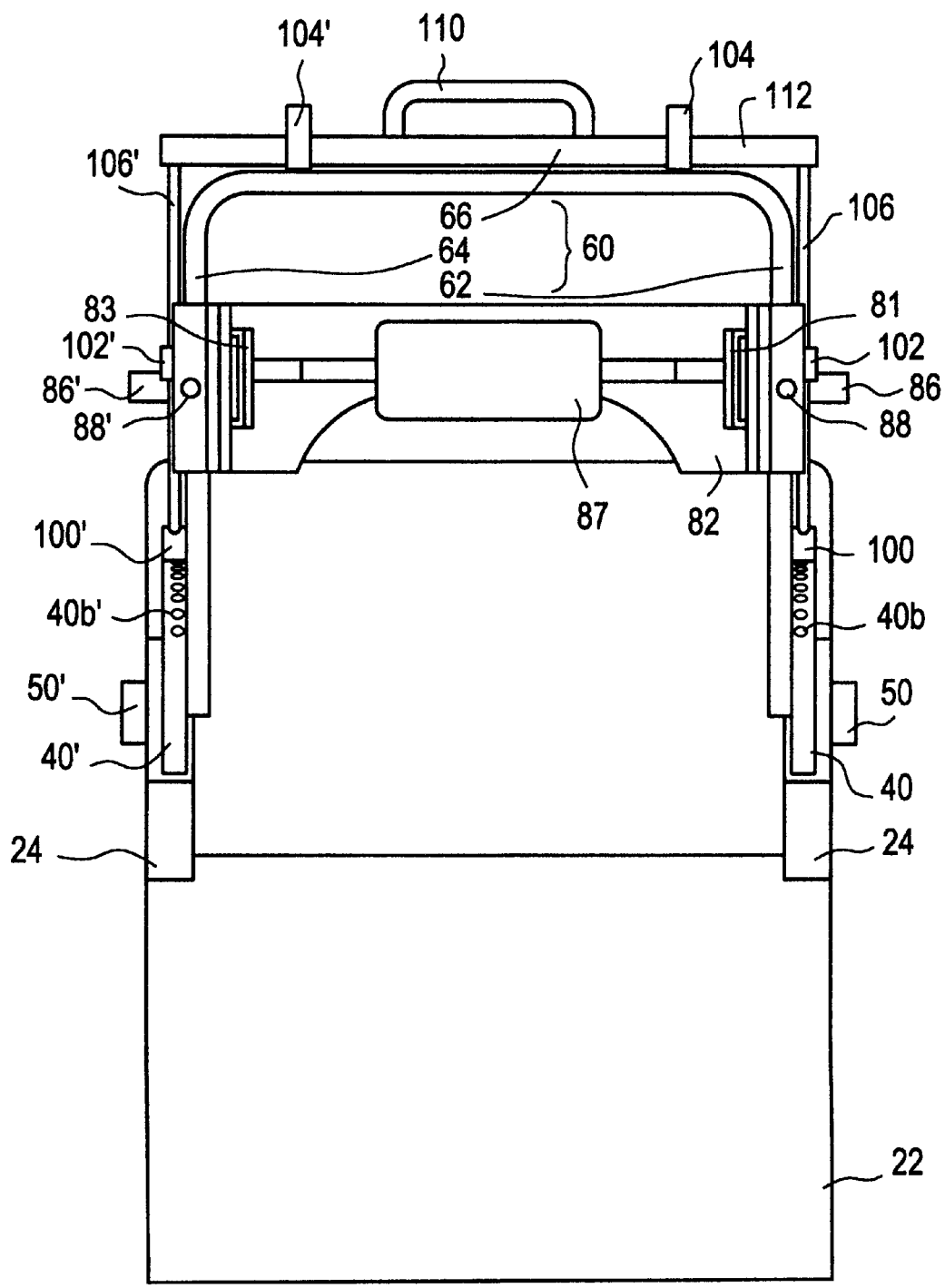
FIG. 13 is a plan view taken in connection with FIG. 11.
Figure 14:
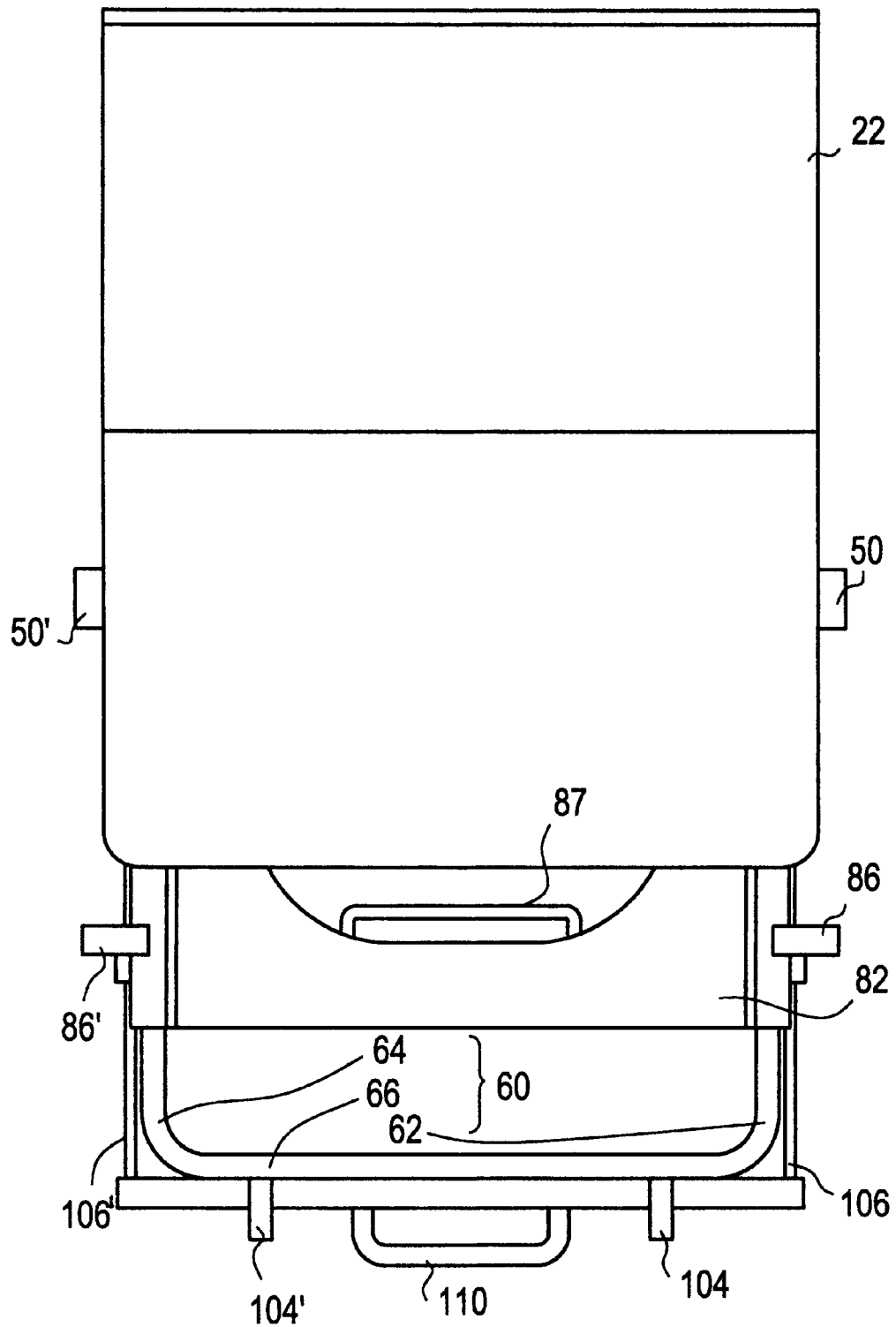
FIG. 14 is a bottom plan view taken in connection with FIG. 11.
Figure 15:
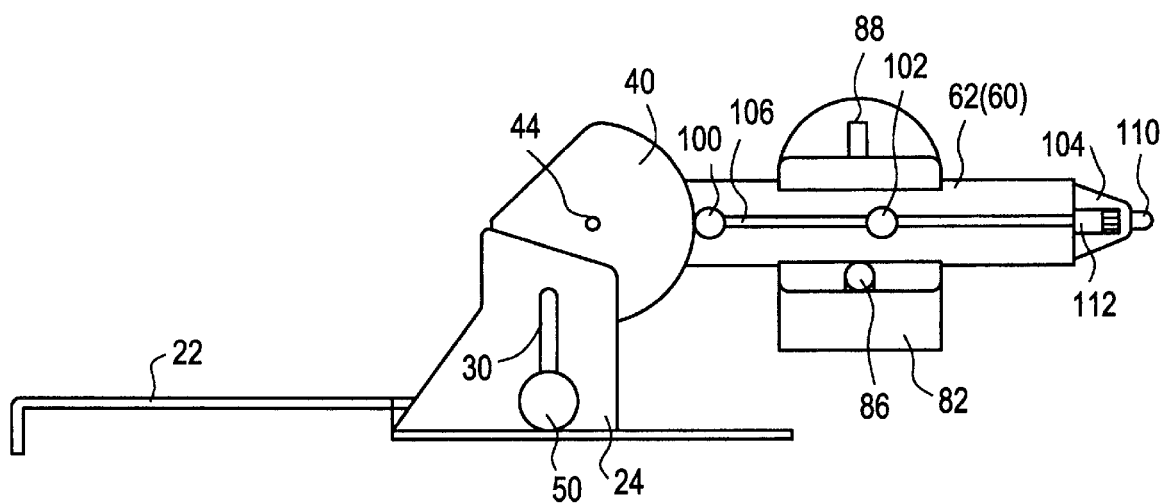
FIG. 15 is a right side view taken in connection with FIG. 11.
Figure 16:
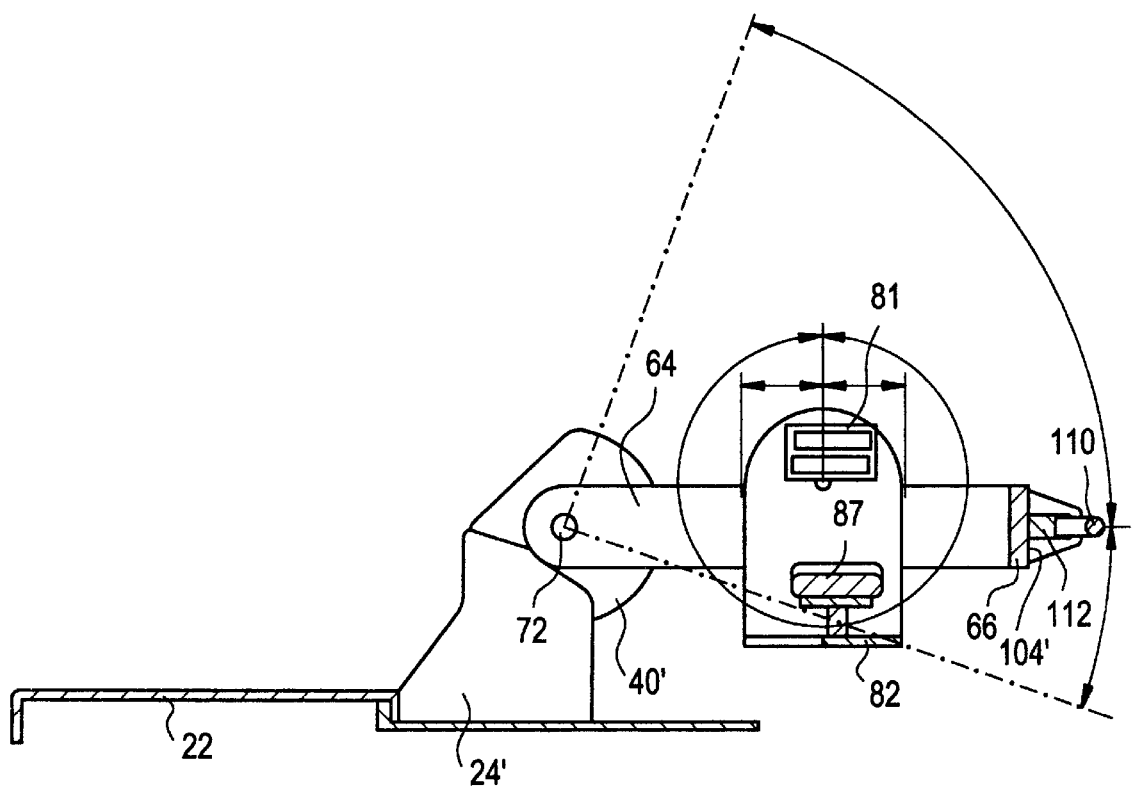
FIG. 16 is a cross-sectional view taken along the line J—J in FIG. 11.

Thus, by inserting/removing a second locking pin 88 through the through hole 80e in the second sliding member 80 into/from one of the lock holes 62e in the first arm portion 62 of the arm 60, the movement of the second sliding member 80, and hence of the head rest 82 attached thereto, along the first and second arm portions 62 and 64 of the arm 60 is prohibited/allowed, respectively. Additionally, FIG. 11 is an elevational view taken in the direction indicated by arrow I, FIG. 12 is a back elevational view taken in connection with FIG. 11, FIG. 13 is a plan view taken in connection with FIG. 11, FIG. 14 is a bottom plan view taken in connection with FIG. 11, FIG. 15 is a right side view taken in connection with FIG. 11 (the left side is symmetrical of the right side.), and FIG. 16 is a cross-sectional view taken along the line J—J in FIG. 11.

The operation in examining a neck bone using the above-constructed neck fixing apparatus with an MRI apparatus will now be described with reference to FIGS. 8 and 9.

Figure 8:
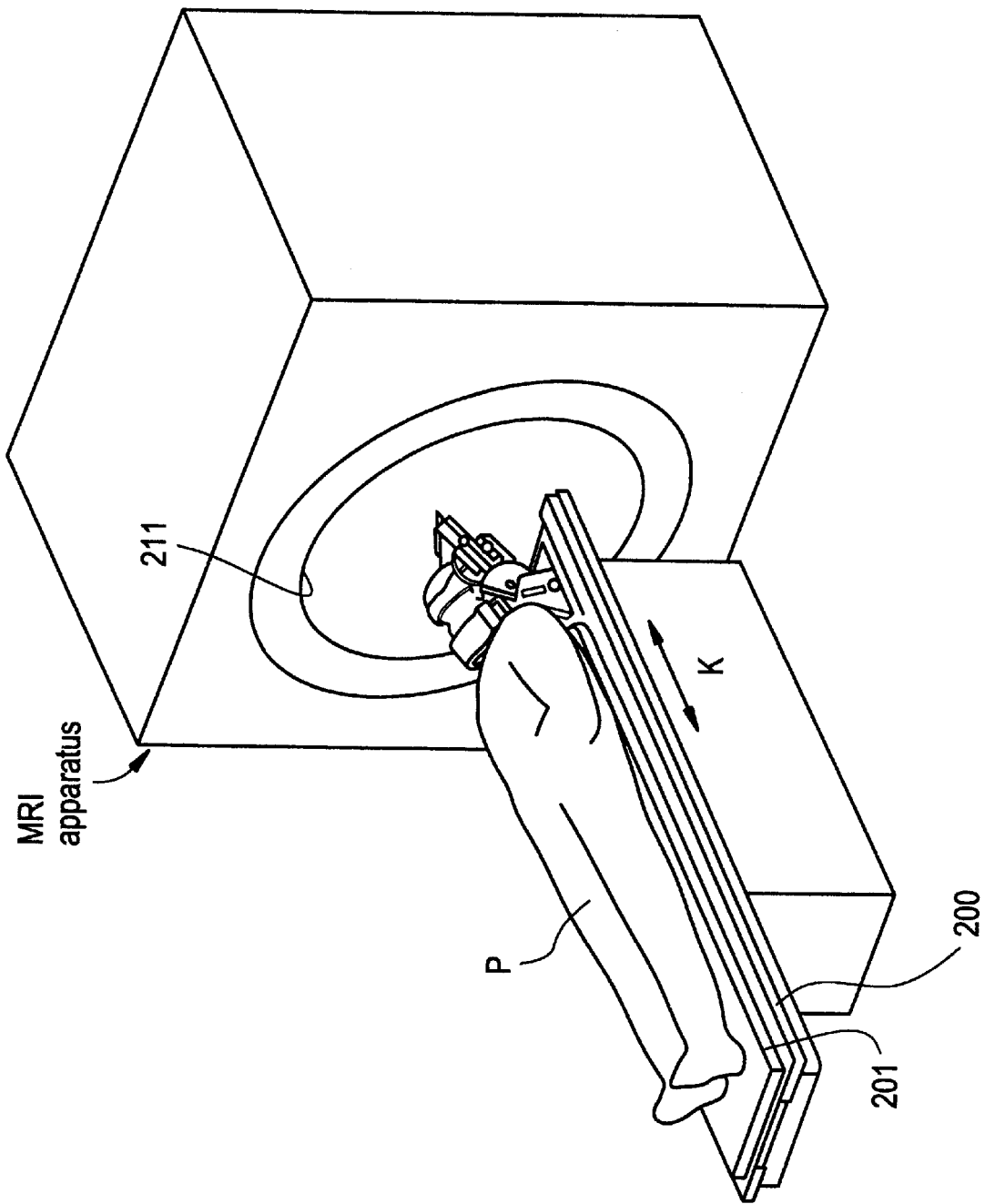
FIG. 8 illustrates the overall construction of an MRI apparatus equipped with a neck fixing apparatus shown in FIG. 2.

In FIG. 8, reference numeral 200 designates a table for mounting a subject P, for carrying the subject P into a bore 211 of an MRI apparatus and also carrying the subject P which has been carried into the bore 211 out from the bore 211 by moving the table 200 in the direction indicated by arrow K.

A mat 201 is mounted on the table 200, and the neck fixing apparatus is disposed on the table 200 with the base 22 inserted between the mat 201 and the table 200.

The subject P is positioned on the mat 201 with the head H mounted on the head rest 82.

Figure 9:
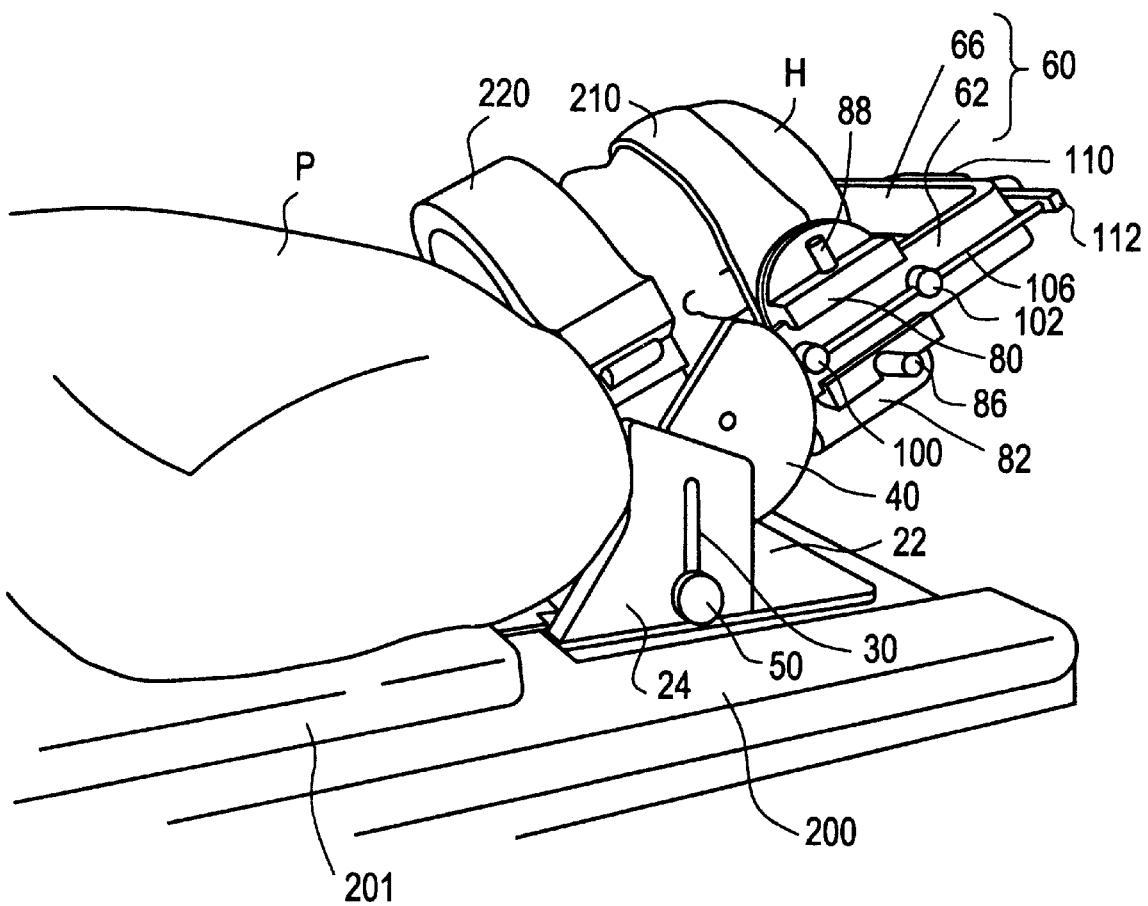
FIG. 9 illustrates a neck fixing apparatus shown in FIG. 2 in operation.

As shown in FIG. 9, the head H of the subject P is fixed to the head rest 82 by a band 210 caught at the band stoppers 81 and 83 on the head rest 82, and a coil 220 is disposed at the neck of the subject P which is a site to be examined.

For the coil 220, a solenoid-type coil is used in the MRI apparatus having a vertical magnetic field, while a saddle-type coil is used in the MRI apparatus having a horizontal magnetic field.

Then, the second locking pins 88 and 88' are removed to move the head rest 82 along the first and second arm portions 62 and 64, and the handle bar 112 is moved away from the bridge 66 of the arm 60 against the contractile force of the elastic member 130. The engagements of the first ends of the locking rods 106 and 106' with the respective lock holes 40b in the first sliding member 40 and 40' are thus released, thereby allowing the arm 60 to rotate around the thread 70.

The arm 60 is then rotated to a desired angular position. At the same time, the head rest 82 moves along the first and second arm portions 62 and 64 following the motion of the neck of the subject P.

After the arm 60 is rotated to the desired angular position, the operational force toward the handle bar 112 is relieved, and as a result, the handle bar 112 moves toward the bridge 66 of the arm 60 bearing against the bridge 66 by the contractile force of the elastic member 130 and the first ends of the locking rod 106 and 106' engage with the corresponding lock holes 40b in the first sliding members 40 and 40'. The rotation of the arm 60 is thus prohibited.

Moreover, the second locking pins 88 and 88' are inserted into and engaged with the lock holes 62e and 62e' in the arm 60 via the through holes 80e and 80e' in the second sliding portions 80 and 80', respectively. The movement of the head rest 82 along the first and second arm portions 62 and 64 of the arm 60 is thus prohibited.

Figure 10A:
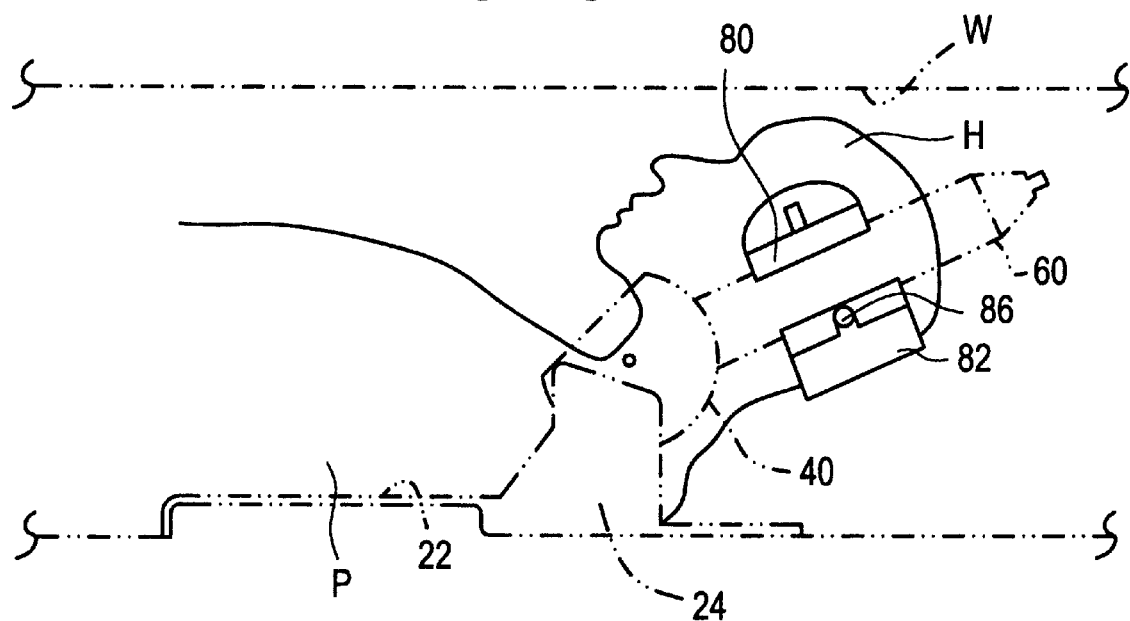
FIGS. 10A, and 10B illustrate the motion of a neck fixing apparatus shown in FIG. 2.
Figure 10B:
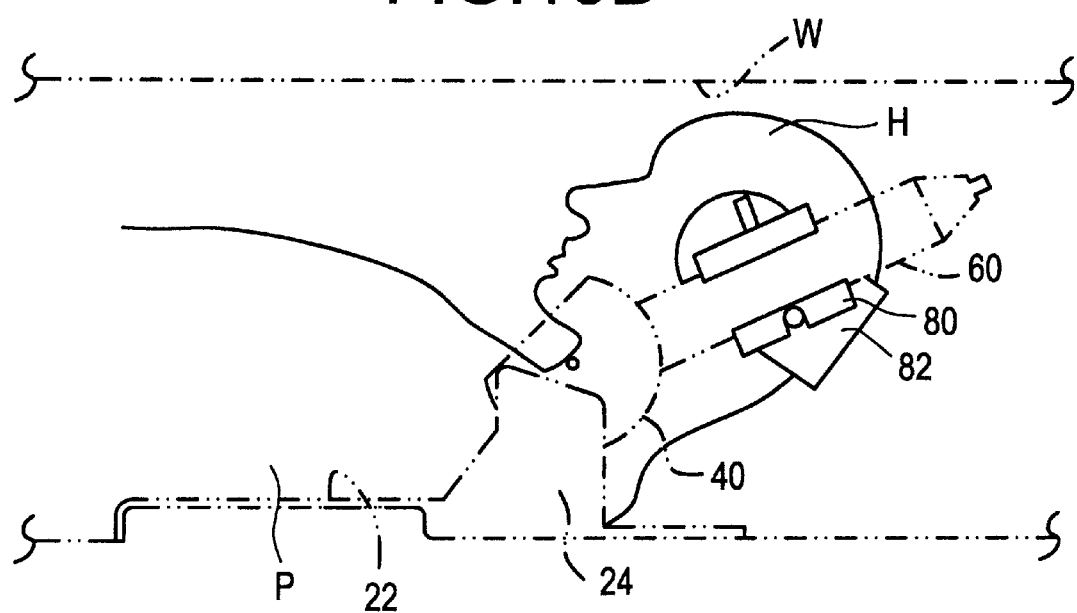

As shown in FIG. 10 (a), when the neck of the subject P needs to be rotated to a substantial extent, the head H of the subject P may be brought close to an inner peripheral surface W of the bore 211 in the MRI apparatus and the additional rotation of the arm 60 may cause the head H of the subject P to meet the inner peripheral surface W of the bore 211 in the MRI apparatus. In such a case, the additional rotation of the neck of the subject P can be accomplished by rotating the head rest 82 with respect to the arm 60, as shown in FIG. 10 (b), preventing the head H of the subject P and the inner peripheral surface W of the bore 211 in the MRI apparatus from touching each other.

In order to rotate the head rest 82 with respect to the arm 60, the first locking pins 86 and 86' are withdrawn and the engagements of the first locking pins 86 and 86' with the respective lock holes 82b and 82b' in the head rest 82 are released. The rotation of the head rest 82 around the threads 91 and 91' with respect to the arm 60 is thus allowed.

After the head rest 82 is rotated to the desired angular position, the first locking pins 86 and 86' are inserted into and engaged with the corresponding lock holes 82b and 82b' in the head rest 82, which makes the head rest 82 again locked. The rotation of the head rest 82 is thus prohibited.

Similarly, when the head H of the subject P reaches close to the inner peripheral surface W of the bore 211 in the MRI apparatus and the additional rotation of the arm 60 may cause the head H of the subject P to meet the inner peripheral surface W of the bore 211 in the MRI apparatus, the first sliding member 40 is moved upwardly or downwardly to bring the head H of the subject P away from the inner peripheral surface W of the bore 211 in the MRI apparatus, thereby allowing the arm 60 to further rotate.

In order to move the first sliding member 40 upwardly or downwardly, the knobs 50 and 50' are loosened, which allows the first sliding members 40 and 40', and hence the arm 60, to move along the long holes 30 and 30' in the posts 24 and 24'.

After moving the arm 60 to the desired height, the movement of the arm 60 is prohibited by driving the knobs 50 and 50'.

According to the above-constructed neck fixing apparatus, since the head rest 82 is constructed to move along the arm 60 in conjunction with the rotation of the arm 60, the head rest 82 on which the head H of the subject P is mounted can be moved along the arm 60 in conjunction with the rotation of the arm 60, and as a result, the discordance between the head H of the subject P and the head rest 82 is avoided and the motion of the head rest 82 and that of the head H of the subject P match with each other.

Even in the case that the head H of the subject P reaches close to the inner peripheral surface W of the bore 211 in the MRI apparatus and the additional rotation of the arm 60 may cause the head H of the subject P to meet the inner peripheral surface W of the bore 211 in the MRI apparatus, the additional rotation of the neck of the subject P can be accomplished by rotating the head rest 82 with respect to the arm 60 and/or by moving the first sliding member 40 upwardly or downwardly.

Many widely different embodiments of the invention may be constructed without departing from the spirit and the scope of the present invention. It should be understood that the present invention is not limited to the specific embodiments described in the specification, except as defined in the appended claims.

We claim:

1. An apparatus for positioning a head of a subject being examined, said apparatus comprising:

a planar base;

a pair of supports slidably mounted on said planar base with a space therebetween;

a U-shaped arm having a pair of sides and an interconnecting end piece disposed at a first end of each side and being rotatably connected to said head supports at a second end of each side;

a head support means comprising a saddle on which said head is mountable and two end portions mounted on said pair of sides of said U-shaped arm so that said head support means is slidable along said pair of sides of said U-shaped arm and so that said head support means is also rotatable around an axis which is transverse to said pair of sides of said U-shaped arm;

means for manually assisting rotation said U-shaped arm and said head support means about said pair of supports connected to said interconnecting end of said U-shaped arm; and means disposed on said pair of supports and connected to said U-shaped arm for rotating said U-shaped arm about said pair of supports.

* * * * *